United States Patent [19]

Kersten et al.

[11] Patent Number: 4,828,892
[45] Date of Patent: May 9, 1989

[54] POLYOLEFIN FILM FOR STEAM STERILIZABLE FLEXIBLE CONTAINERS

[75] Inventors: Jean Kersten, Villers St. Amand; Leon Lecomte, Rhismes, both of Belgium

[73] Assignee: Baxter International Inc., Deerfield, Ill.

[21] Appl. No.: 855,279

[22] Filed: Apr. 24, 1986

Related U.S. Application Data

[63] Continuation of Ser. No. 680,459, Dec. 11, 1984, abandoned, which is a continuation-in-part of Ser. No. 655,494, Sep. 28, 1984, abandoned.

[51] Int. Cl.⁴ .................... B65D 30/08; B32B 7/02; B32B 27/08
[52] U.S. Cl. .................... 428/35.2; 383/109; 428/212; 428/213; 428/216; 428/218; 428/516
[58] Field of Search ............ 428/35, 218, 216, 516, 428/212, 213; 383/109

[56] References Cited

U.S. PATENT DOCUMENTS 4,022,646  5/1977  Casey ................................ 428/218
4,210,686  7/1980  Gajewski et al. .................. 428/516

FOREIGN PATENT DOCUMENTS 699406  12/1964  Canada .

Primary Examiner—Ellis P. Robinson
Assistant Examiner—James J. Seidleck
Attorney, Agent, or Firm—Paul C. Flattery; Robert H. Barrett; Paul E. Schaafsma

[57] ABSTRACT

A film structure for a steam sterilized container capable of containing a liquid to be maintained and removed under sterile conditions is provided. The film has at least two polyolefin layers, the outer layer having a greater density and softening temperature than the inner layer.

9 Claims, 2 Drawing Sheets

POLYOLEFIN FILM FOR STEAM STERILIZABLE FLEXIBLE CONTAINERS

This is a continuation of application Ser. No. 680,459, filed Dec. 11, 1984, now abandoned which is a continuation-in-part of copending U.S. patent application Ser. No. 655,494, filed on Sept. 28, 1984, now abandoned.

BACKGROUND OF THE INVENTION

This invention relates to a film structure for flexible containers. In particular, this invention relates to a polyolefin film for steam sterilizable containers capable of containing a liquid to be maintained and accessed under sterile conditions.

Flexible, collapsible liquid containers are utilized in the medical industry for parenteral solutions and the like. Typically, these containers consist of a liquid containing body defined by heat sealed walls. Because these containers are utilized to contain fluids that are introduced intravenously into patients, it is necessary that the containers: are essentially transparent; are flexible; essentially free of extractables; and are sterilizable.

Various materials and structures have been utilized for parenteral solution containers. The materials that have been utilized include polyethylene, polyvinyl chloride, polypropylene, poly(ethylene methyl acrylate), and other copolymers.

One of the problems of the prior art film is that if these containers are to be steam sterilized, it is necessary that the outer layer of the film has a sufficiently high softening temperature so that it does not substantially deform during sterilization. In the prior art, creating a steam sterilizable outer layer usually resulted in sacrificing some other desired property. For example, to achieve the desired thermal resistance when a polyolefin is utilized, the thickness of the polyolefin has been increased to such an extent that clarity was impaired.

It has also been found that mechanical properties like impact strength decrease with an increase in the softening temperature of the polyolefin structure. Accordingly, if a polyolefin structure with a higher softening temperature is utilized, an increase in the thickness of the polyolefin film structure is required. This increase in thickness results in poor optical properties and a lack of flexibility that results in an increase in the size of the container. Moreover, because the flexible container is created by the inner surfaces of the polyolefin film being heat sealed together, the increase in thickness and/or softening temperature increases the time necessary for effectuating these seals. This in turn increases the duration of the production cycle necessary to create the flexible container, thereby resulting in a less economical flexible container.

Another example of a film structure that has not provided entirely satisfactory results is a polyethylene film structure. Because of polyethylene's susceptability to deformation, lower sterilization temperatures have been utilized for films constructed from polyethylene. The use of lower sterilization temperatures lengthens the total cycle duration for the production of flexible containers from polyethylene. This results in a less economical production cycle and accordingly a more expensive container.

Thus, there is a need for a new polyolefin film structure for creating steam sterilizable, flexible containers that overcomes the problems of the prior art.

SUMMARY OF THE INVENTION

The present invention provides a polyolefin film for steam sterilization containers capable of containing a liquid to be maintained and extracted under sterile conditions. The film comprises two polyolefin layers, the first layer having a greater density than the second layer, to provide a film that can be used to create a steam sterilizable container. The outer layer typically has a greater softening temperature than the inner layer.

Preferably, the first or outer layer is constructed from a high density polyethylene, and the second or inner layer is constructed from a medium density polyethylene.

In another embodiment the film comprises three layers. The three layer film includes an outer layer constructed from a high density polyethylene and a middle and inner layer constructed from a medium density polyethylene; the outer layer having a higher softening temperature than the middle and inner layer.

Accordingly, it is an advantage of the present invention to provide a polyolefin film that can be steam sterilized yet provides a flexible container with sufficient clarity, strength, and can be heat sealed together on its inner edges.

Another advantage of the present invention is that it provides a two layer polyolefin film comprising a first layer having a greater softening temperature than a second layer and therefore can be utilized to create bags that can be steam sterilized.

A still further advantage of the present invention is that it provides a polyolefin structure that does not substantially melt or distort when steam sterilized at a temperature of approximately 115° C. to about 121° C.

Another advantage of the present invention is that it provides a two layer polyethylene film structure capable of creating containers for holding liquids to be maintained and extracted under sterile conditions.

Another advantage of the present invention is that it provides a three layer polyolefin film structure wherein the first layer has a greater density and softening temperature than the second and third layers.

Another advantage of the present invention is that it provides a three layer polyethylene film wherein the outer layer can be steam sterilized at temperatures of approximately 115° C. to about 121° C. without substantially melting or distorting.

A still further advantage of the present invention is that it provides a method of creating a film structure that substantially reduces the number of gel breach defects that occur during extrusion.

Additional features and advantages are described in, and will be apparent from, the Detailed Description of the Presently Preferred Embodiments and from the drawings.

DETAILED DESCRIPTION OF THE PRESENTLY PREFERRED EMBODIMENTS

The film structure of the present invention is utilized to make steam sterilizable flexible containers capable of containing a liquid to be maintained and accessed under sterile conditions. These containers typically consist of a liquid containment body defined by thermally sealed walls. An example of such a container is the VIAFLEX ® container for parenteral solutions marketed by Travenol Laboratories, Inc. of Deerfield, Ill.

In one embodiment of the invention, two bonded polyolefin layers are utilized to produce the film structure of the present invention. The layers may be constructed from any appropriate polyolefin known in the art to create flexible film including, polyethylene, poly-(ethylene-vinyl acetate) and polypropylene. The preferred polyolefin is linear polyethylene.

The structure of the desired polyolefin is based on three considerations: the density of the polyolefin; the softening point of the polyolefin; and the relative thickness of the layer of polyolefin. Because the first layer of the polyolefin will be utilized as the outer layer of the bag, this layer must be capable of being steam sterilized without suffering substantial distortion or melting. Moreover, because the second layer is utilized as the inner layer of the bag, and therefore must be sealed to a corresponding layer, it is important that this layer can readily melt and thereby heat seal.

Figure 1:
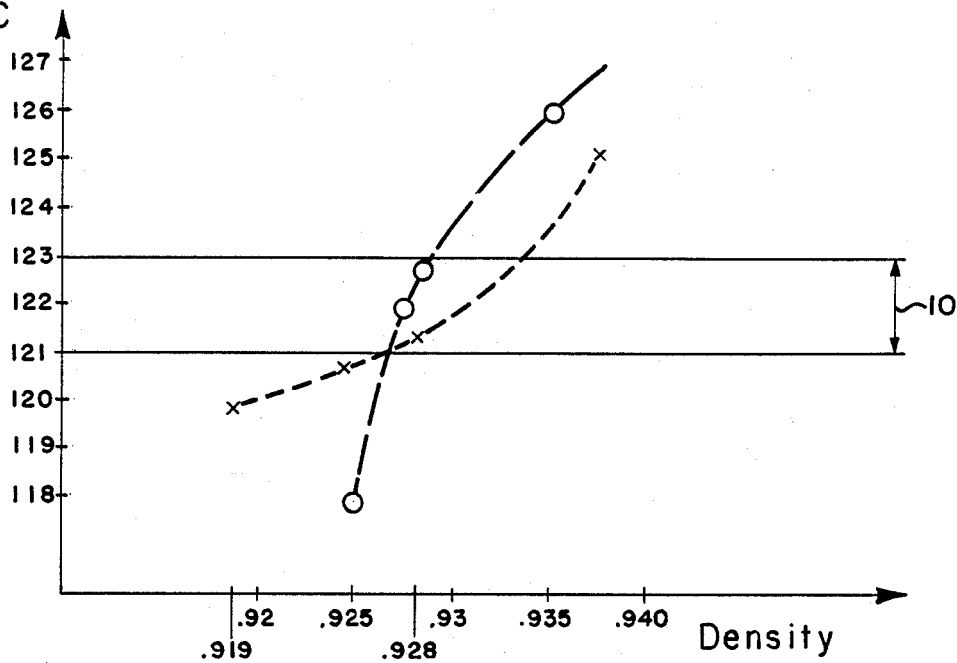
FIG. 1 illustrates a graph of the density of the film versus the softening temperature of the film.

It has been found that the film structure should be chosen based on a function of the density of the polyolefin versus the melting point of the polyolefin. FIG. 1 illustrates a graph utilizing these parameters. It has been found that if one graphs these parameters, one gets a "window" 10 as shown in FIG. 1. It is within this window that the preferred film structures fall. "X" refers to polyethylene comonomers with butene; "O" refers to polyethylene comonomers with octene.

Figure 2:
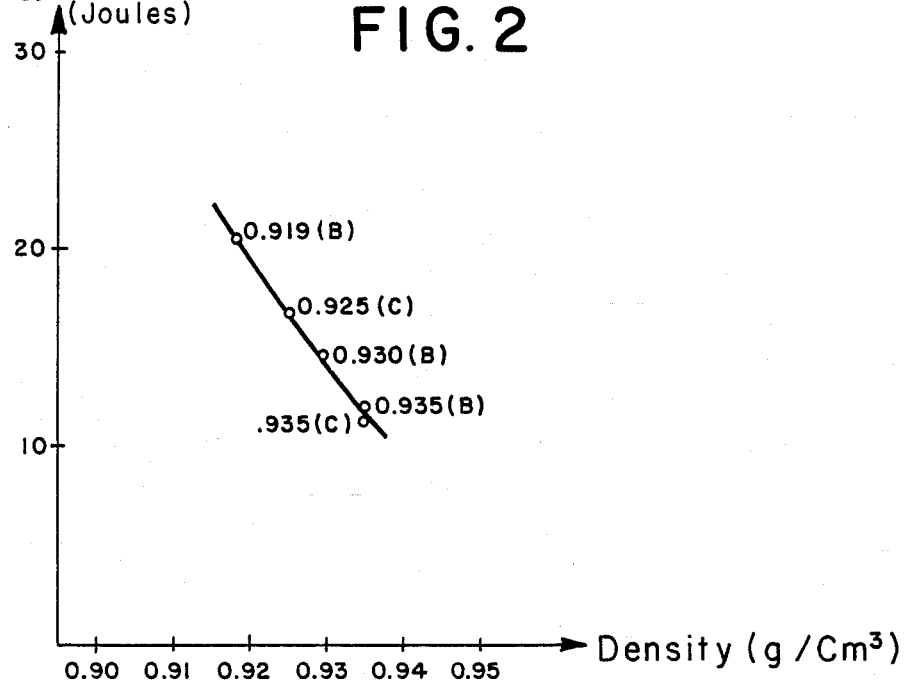
FIG. 2 illustrates a graph of the density of the film versus the impact strength of the film.

FIG. 2 illustrates a graph of the density of polyethylene film versus its impact strength. As illustrated, the impact strength of the film is related to the density of the film. The density of a 150 micron unsterilized film of polyethylene was tested; the impact strength is measured in Joules. The impact strength was determined by dropping filled containers constructed from the polyethylene film. (B) refers to blown polyethylene film, (C) refers to cast polyethylene film.

Figure 3:
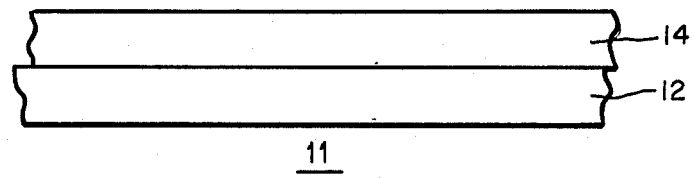
FIG. 3 illustrates a schematic cross sectional view of an embodiment of the film of this invention.

An example of a two layer polyolefin structure that has been found to provide good results as a film for creating a flexible container is as follows. As illustrated in FIG. 3, the film 11 comprises a first layer 12 constructed from a high density polyethylene. As used in this disclosure, high density means that the density of the structure is between approximately 0.935 and 0.965 gm/cc. The second layer 14, is bonded to the first layer, and is constructed from medium density polyethylene. As used in this disclosure, medium density means that the density of the structure is between approximately 0.917 and 0.930 gm/cc. Preferably the density of the first polyethylene layer is approximately 0.95 to 0.96 gm/cc, and the density of the second layer is approximately 0.92 to 0.93 gm/cc. In a most preferred embodiment the density of the first polyethylene layer is about 0.952 gm/cc and the density of the second polyethylene layer is about 0.928 gm/cc. The film of FIG. 3 may be made by a conventional coextruded process.

Preferably the linear medium density polyethylene for constructing the film of this invention is a polyethylene copolymer. Preferably, the linear medium density polyethylene contains 2 to 5 weight % of butene or 2 to 5 weight % of octene as copolymer. Because of its greater impact strength polyethylene with 3% octene is preferred. Preferably the polyethylene for constructing the film of this invention is cast polyethylene.

To provide a film that is capable of forming a flexible container that can be steam sterilized, the first polyethylene layer 12 preferably has a softening temperature (Vicat softening point) between about 110° C. to 130° C. Preferably, the second polyethylene layer has a softening temperature (Vicat softening point) between about 100° C. to 120° C. The resulting multilayer structure provides a film that offers the following advantages over a monolayer polyolefin film: much higher impact strength than monolayer films with an overall higher density; improved optical characteristics than monolayer films with an overall higher density; better surface properties than monolayer films with an overall lower density; superior thermal resistance properties than monolayer films with an overall lower density; and a stronger seal strength than, monolayer films with an overall higher density. Moreover, the flexible container constructed from preferred films of this invention can be steam sterilized at a temperature of approximately 115° C. to about 121° C. without suffering substantial melting or distortion.

Preferably, the thickness of the first polyethylene layer 12 is approximately 20 to about 25 microns. The thickness of the second polyethylene layer 14 is preferably approximately 110 to about 135 microns. This provides a film construction with the proper balance of properties to provide the advantages set forth above.

Figure 4:
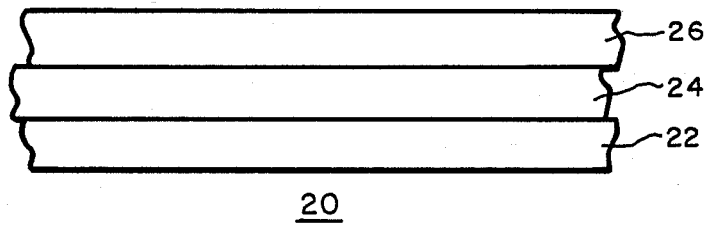
FIG. 4 illustrates a cross sectional view of a further embodiment of the film of this invention.

In a further preferred embodiment, illustrated in FIG. 4, the film structure 20 of the present invention comprises three polyolefin layers. The first polyolefin layer 22 has a greater density and softening point than the second and third polyolefin layers 24 and 26. Preferably the second and third polyolefin layers 24 and 26 have substantially the same density and softening temperature.

It has been found that a three layer polyolefin film with the following structure provides satisfactory results as a flexible container. The first layer 22 is constructed from a high density polyethylene with a preferred density of approximately 0.95 to 0.96 gm/cc. The second layer 24 is constructed from a medium density polyethylene with a preferred density of approximately 0.92 to 0.93 gm/cc. The third layer 26 is constructed from a medium density polyethylene with a preferred density of between approximately 0.92 and 0.93 gm/cc. Preferably, the softening temperature of the first polyethylene layer 22 is approximately 110° C. to 130° C.; and the softening temperature of the second and third polyethylene layers 24 and 26 is approximately 100° C. to 120° C.

In a most preferred embodiment, the first layer 22 of polyethylene has a density of approximately 0.952 gm/cc and the second and third layers of polyethylene have a density of approximately 0.928 gm/cc.

Preferably the thickness of the first polyethylene layer 22 is approximately 20 to about 25 microns and the thickness of the second and third polyethylene layers 24 and 26 is 100 to about 135 microns. Preferably the second polyethylene layer 24 has a thickness of approximately 80 to about 90 microns and the third polyethylene layer 26 has a thickness of approximately 30 to about 50 microns.

The film structure 20 of the three layer film of the present invention provides a film that offers the advantages mentioned above over monolayer polyolefin films. Accordingly, it produces a film structure with good clarity, good surface properties, is steam sterilizable at temperatures of 115° C. to 120° C., and provides an inner layer that can be readily heat sealed.

Preferably, the film structure of this invention is manufactured by coextrusion. If a three layer polyethylene structure is utilized, the middle layer may be constructed from a "regrind" material. Because the middle layer is constructed from a regrind material this offers an advantage from a migration standpoint. This is due to the fact that the regrind is not directly in contact with the solution. Moreover, this construction provides a film with increased sealability.

By utilizing a three layer film structure the chances of defects in the film due to a gel breach are substantially lessened. A gel breach is a defect occurring because of unfused particles of resin.

The polyolefin film of this invention may preferably contain the following additives: antioxidants; antiblocking agents; neutralizers (particularly metallic neutralizers such as zinc stearate and calcium stearate); lubricants; stabilizers; and slip agents as required for processing. Preferably the high density polyethylene contains the following additives in the following percentages: a maximum of 0.15% antioxidant; a maximum of 100 ppm of antiblocking agents or slip agents; a maximum of 1500 ppm neutralizers. Preferably the medium density polyethylene contains the following additives in the following percentages: a maximum of 0.15% antioxidant; a maximum of 100 ppm of antiblocking agents or slip agents; a maximum of 1500 ppm neutralizers. These additives provide required processing capability to the film structure.

By way of example, and not limitation, an example of the film of this invention will now be set forth.

EXAMPLE

The film is a coextrusion having an out layer, a middle layer, and an inner layer. The middle layer and inner layer are constructed from the same material. The overall film structure comprises: 99.5% by weight linear polyethylene; 0.15% by weight Irganox 1076; 0.05% by weight zinc stearate; a maximum of 0.19% by weight silica; and a maximum of 0.10% by weight Erucamide. The zinc stearate acts as a lubricant, the silica acts as an antiblocking agent, and the Erucamide as a slip agent.

Referring now to the individual layers of the film, the outside layer comprises: 99.85% by weight of a polyethylene resin sold under the name Stamylex M 7058 by DSM Belgium S.A., Brussels, Belgium; a maximum of 0.095% by weight Irganox 1076 sold by Ciba-Geigy; and a maximum of 0.05% by weight zinc stearate sold by U.C.B. Products Chimiques. The polyethylene resin has a density of approximately 0.955 gm/cc.

The inner and middle layers comprises: 98% by weight linear medium density polyethylene and a maximum of 1.95% by weight of a masterbatch. The linear medium density polyethylene comprises: 99.84% by weight of a blend of polyethylene resins, the blend of polyethylene comprising approximately 95–80% by weight Stamylex M 2046 sold by DSM and having a density of approximately 0.9285 and 5–20% by weight Stamylex M 7058; a maximum of 0.095% by weight Irganox 1076 sold by Ciba-Geigy; and a maximum of 0.05% by weight of zinc stearate sold by U.C.B. Products Chimiques. The masterbatch comprises: 85% by weight linear medium density polyethylene, the polyethylene being the above-stated blend; 10%±1% by weight silica sold by Manville de France, under the name Celite 499; and 5% ±0.5% by weight Erucamide sold by Croda, France S.A. under the name Eracamide E.R.

Figure 5:
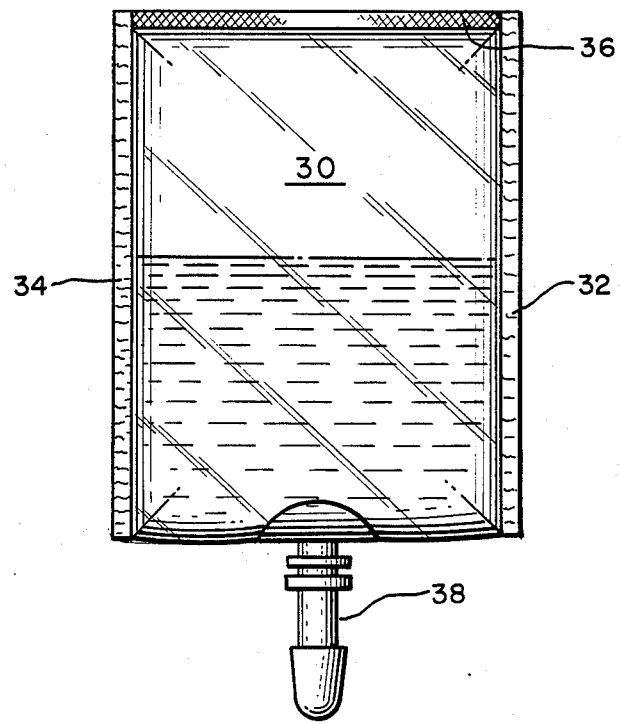
FIG. 5 illustrates a container constructed from the film of this invention.

As illustrated in FIG. 5, the film of this invention may be used to produce a container 30 for housing a product to be maintained and accessed under sterile conditions. The container 30 includes side seals 32 and 34, a top seal 36 and a fitment 38. The film of this invention is constructed so that it can be run on a production machine to make a container 30. An example of such a production machine is a form, fill, and seal packaging machine.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A flexible, sterilizable container capable of containing a fluid and maintaining sterility, the container having a body portion having walls sealed on at least two sides, the body portion being constructed from a three layer film comprising:
   an outer layer for defining an outer surface of the container constructed from a high density polyolefin;
   an inner layer for defining an inner surface of the container constructed from a medium density polyolefin;
   the middle layer being bonded between the inner and outer layer;
   the combined thickness of the middle and inner layers being greater than the thickness of the outer layer; and
   the film defining a container that does not substantially melt or distort when the container is steam sterilized at a temperature of approximately 115° C. to about 121° C.

2. The container of claim 1 wherein the outer layer has a higher softening temperature than the inner layer.

3. The container of claim 1 wherein:
   the outer layer is a polyethylene having a density approximately 0.95 to 0.96 gm/cc; and
   the middle and inner layer are polyethylenes having a density of approximately 0.92 to 0.93 gm/cc.

4. The container of claim 3 wherein:
   the thickness of the outer layer is approximately 20 to 25 microns; and
   the combined thickness of the middle and inner layers is 110 to 135 microns.

5. The container of claim 4 wherein:
   the thickness of the middle layer is approximately 30 to 50 microns; and
   the thickness of the inner layer is 80 to 90 microns.

6. The container of claim 1 wherein the density of the middle and inner layers are substantially the same.

7. The container of claim 1 wherein:
   the outer layer has a softening temperature of approximately 110° C. to 130° C.;
   the middle layer has a softening temperature of approximately 100° C. to 120° C.; and
   the inner layer has a softening temperature of approximately 100° C. to 120° C.

8. The container of claim 1 wherein the film is produced by coextrusion and the middle layer is constructed from a regrind material.

9. The container of claim 1 wherein the polyolefin is a polyethylene.

* * * * *

UNITED STATES PATENT AND TRADEMARK OFFICE
CERTIFICATE OF CORRECTION

PATENT NO. : 4,828,892

DATED : May 9, 1989

INVENTOR(S) : Jean Kersten et al

It is certified that error appears in the above-identified patent and that said Letters Patent is hereby corrected as shown below:

Column 5, line 48, "99.85%" should read -- 99.84% --.

Signed and Sealed this

Twenty-seventh Day of March, 1990

*Attest:*

JEFFREY M. SAMUELS

*Attesting Officer*      *Acting Commissioner of Patents and Trademarks*

UNITED STATES PATENT AND TRADEMARK OFFICE
CERTIFICATE OF CORRECTION

PATENT NO. : 4,828,892

DATED : May 9, 1989

INVENTOR(S) : Jean Kersten et al.

It is certified that error appears in the above-identified patent and that said Letters Patent is hereby corrected as shown below:

> In Column 6, after line 27, in Claim 1, a portion of Claim 1 has been erroneously deleted. The missing portion reads -- a middle layer constructed from a medium density polyolefin; -- and should appear after the text currently at Column 6, lines 25 - 27 which states ...an outer layer for defining an outer surface of the container constructed from a high density polyolefin;...

Signed and Sealed this

Twelfth Day of February, 1991

*Attest:*

HARRY F. MANBECK, JR.

*Attesting Officer*    *Commissioner of Patents and Trademarks*